(12) United States Patent
Khan et al.

(10) Patent No.: US 6,248,582 B1
(45) Date of Patent: Jun. 19, 2001

(54) GENE DELETED RECOMBINANT FELV PROVIRAL DNA FOR PRODUCTION OF VACCINES AGAINST FELV

(76) Inventors: Imran Khan, 1660 Drew Ave. #66, Davis, CA (US) 95616; Charles J. York, 26217 Cielito Lindo Rd., Winters, CA (US) 95694

( * ) Notice: Subject to any disclaimer, the term of this patent is extended or adjusted under 35 U.S.C. 154(b) by 0 days.

(21) Appl. No.: 09/167,796

(22) Filed: Oct. 7, 1998

Related U.S. Application Data (60) Provisional application No. 60/061,442, filed on Oct. 8, 1997.

(51) Int. Cl.[7] .............................. C12N 15/00; C12Q 1/70; A61K 38/00; A61K 39/42; C07H 21/02
(52) U.S. Cl. ................................ 435/320.1; 435/5; 435/6; 530/324; 536/23.1; 424/160.1; 424/207.1
(58) Field of Search .................... 435/5, 6, 320.1; 530/324; 536/23.1; 424/160.1, 207.1

(56) References Cited

U.S. PATENT DOCUMENTS 4,794,168   12/1988   Elder et al. ........................... 530/324
5,763,209    6/1998   Sukhatme et al. .................. 435/69.1

OTHER PUBLICATIONS

Tartaglia, J., et al., "Protection of Cats against Feline Leukemia Virus by Vaccination with a Canarypox Virus Recombinant, ALVAC–FL" *J. of Virology*, 67(4):2370–2375 (1993).

Noronha, C., et al., "Generation and Role of Defective Proviruses in Cytopathic Feline Leukemia Virus (FeLV–FAIDS) Infections" *J. of Virology*, 70(1):359–367 (1996).

*Primary Examiner*—Hankyel T. Park
(74) *Attorney, Agent, or Firm*—Townsend and Townsend and Crew LLP (57) ABSTRACT

Methods and compositions for a vaccine against feline leukemia are disclosed.

36 Claims, 4 Drawing Sheets

LANE 1: FeLV (FL74) - WHOLE VIRUS (10 ug TOTAL PROTEIN)
LANE 2: BHK CELLS TRANSFECTED WITH pND - VECTOR ALONE
LANE 3 & 5: BHK CELLS TRANSFECTED WITH OTHER FeLV CONSTRUCTS
LANE 4: BHK CELLS TRANSFECTED WITH pIK102
LANE 6: NON-TRANSFECTED BHK CELLS

GENE DELETED RECOMBINANT FELV PROVIRAL DNA FOR PRODUCTION OF VACCINES AGAINST FELV

This application claims benefit to U.S. provisional 60/061,442 filed Oct. 8, 1997.

FIELD OF INVENTION

This invention relates to the field of viral vaccines, particularly to use and production of genetically deleted feline leukemia virus proviral DNA that produce nonreplicating virus particles in vivo. The DNA can also be used to produce immunogenic polypeptides derived from the FeLV genome. These vaccines are especially useful against FeLV and the disease associated with FeLV.

BACKGROUND OF THE INVENTION

Feline leukemia virus (FeLV) is an exogenous type C retrovirus of the Retrovirdae virus family. It is associated with multiple immunosuppressive diseases specifically with the lymphoreticular disease, including lymphosarcoma, leukemia, aplastic anemia, myelodysplasis and feline acquired immunodeficiency syndrome Hardy et al., *Cancer Res.* 36:582, 1976; Hardy Feline Leukemia Virus, Hardy, Essex, McCelland, eds. (Elsevier/North Holland, 1980), pp.3–31; Hoover, Rojko, Olsen, *Feline Leukemia,* Olsen, ed. (CRC Press, Boca Raton, Fla., 1980), pp.32–51; Hardy and Essex, *Prog. Allergy* 37:353, 1986). FeLV isolates are divided into three subgroups A, B, and C based on their interference and neutralization patterns (Sarma et al. *Virology* 44:352–358 (1971); Donahue, P. R. et. al. *J. Virol.* 66:722–731 (1988); Jarret, O. et. al. *Int. J. Cancer* 21:334–387 (1978). FeLV-A is found in every isolate in nature either alone or in combination with B and C subgroups and is considered to be the subgroup most responsible for viremia and the latent carrier state. FeLV-B is found in about 40% of all infections whereas FeLV-C is found in only 1% of infections and occurs in combinations with B and A subgroups. Because FeLV-A demonstrates a more restricted cell tropism in vitro and tends to be less pathogenic, the presence of subgroup A in all infections makes it the obvious target for prevention of FeLV infection (Loar, A. S. Vet. Cl. N. Amer. 23:193–211).

Pharmaceutical compounds that will eliminate or control virus replication once the virus is introduced in cats have not been well tested; however, several preventative vaccines have been developed. FeLV vaccines are sold under at least 8 different trade names including at least 3 combination products from 4 different manufacturers. The product tradenames include: Leukocell and Leukocell 2 (Pfizer), Leukogen (Virbac), Gentivac (Schering(Coopers), RM Leucat (Rhone-Merieux/MERIAL), Fevaxyn (Schering/Solvay), FeloVax (Fort Dodge), and VacSYN/FeLV (Symbiotics). These vaccine preparations include infected cell extracts, whole virus preparations, and recombinant envelop protein subunit vaccines. In addition to these commercial vaccines, there are several disclosures that describe other possible methods for immunization against FeLV including treatments with recombinant derived FeLV peptides alone or in combination with attenuated virus or proviral DNA preparations (U.S. Pat. Nos. 4,701,416, 4,876,089, 5,152,982, 4,789,702, EPO 0247904, PCT U.S.85/02319), virus vectors expressing FeLV gene products (U.S. Pat. Nos. 4,957,865, 5,324,664, PCT U.S. Ser. No. 88/02816, GB90/00116, U.S. Ser. No. 92/08427), peptide vaccines containing smaller components of full length gene products (U.S. Pat. Nos. 4,663,436, 4,794,168), self-assembled replication-deficient virus particle production, and vector produced non-replicative virus particle production (PCT U.S. Ser. No. 93/09070).

Despite the variety of FeLV approaches to vaccine development and utilization there are still important and pertinent features that the present preventative or therapeutic treatments do not provide. None of the vaccines utilize an antigen or vaccination method that allows for cross protection against all field isolates and subgroups nor do they include components that provide protection against other immunosuppressive or immunodeficient viruses such as FIV or FIPV. Vaccines, which use non-purified virus or infected cell material have inconsistencies in the amount of virus-associated material that exist in each vaccine preparation. As a consequence there is variability with these vaccines in both delayed and immediate site reactions. In addition, retroviruses are notoriously low producers in cell culture and are relatively unstable in unprocessed or non-cryopreserved forms, which contributes to limited storage periods of FeLV components in manufacturing. As a consequence the FeLV is often the limiting antigen when attempting to develop combination vaccines with other infectious disease agents of felines. In general, there is also an inability to determine and to discriminate subgroups A, B and C within the vaccine and manufacturing material. Because all existing FeLV vaccines on the market are inactivated (killed) preparations, two and sometimes three doses are recommended for active immunization of cats. Because of these limitations within the present commercial products and continued demands by the clinician for managing and controlling immunosuppressive disease there is a need in the art for improved methods for immunization against FeLV and associated disease.

The present invention is provided to address all of the above needs. In particular it provides a FeLV vaccine that cannot only deliver an efficacious dose of FeLV in a convenient administration, but can also be manufactured in a more consistent manner than previous art. In addition, the invention described here is derived from a new isolate of FeLV (BTI-FeLV-A) taken from a cat in Fair Oaks, Calif. This virus is subgroup A has not been described before and represents a virus isolate that has evaded or is not controlled by current vaccination programs.

SUMMARY OF THE INVENTION

The present invention provides compositions and methods for inducing immune responses against FeLV. In some embodiments, the compositions comprise a nucleic acid molecule comprising a truncated FeLV genome. The nucleic acids comprise an env gene from FeLV from BTI-FeLV-A. The nucleic acid can be incorporated into an expression vector according to well known methods. This expression vector can be used to vaccinate cats against FeLV and FeLV associated diseases; this vector can also be amplified in bacterial hosts so as to allow for consistent and reliable production of the gene product under fermentation parameters and DNA purification methods.

In one aspect of the invention a bacterial plasmid DNA has been genetically recombined to a provirus DNA of FeLV that has been truncated in the polymerase (pol) gene to remove the capability of producing new genetic templates of FeLV-genome specificity. In an embodiment, the proviral DNA has been isolated from a new isolate of feline leukemia virus that has homology to subtype A based on partial sequence of the envelope gene. In another embodiment, the FeLV proviral DNA has been debilitated in that the long terminal repeat (LTR) on the 3' end and 5' ends of the genome have been removed from the proviral DNA. In another embodiment the integrase functions of the polymerase (Po) gene have been deleted. In another embodiment the proviral DNA has a cytomegalovirus (CMV) early promoter region on the 5' end of the genome to drive expression of the FeLV viral genes and a bovine growth hormone gene (BGH) poly A addition signal recombined at the 3' end of the genome to terminate viral mRNA synthesis. In another embodiment the modified FeLV proviral DNA encodes and can express the entire gag and envelope gene (env) products of FeLV. Another aspect of this invention is the production of non-replicating virus particles in vivo from the intramuscular injection of the purified plasmid encoding the truncated form of FeLV proviral DNA. In an embodiment, the non-replicating viral particles have the following characteristics:

they contain no detectable FeLV genomic RNA but retain specificity of the group specific antigen (gag) and envelope antigens (env) of the virus particle.

the virus particles produced from the truncated form of FeLV proviral DNA are capable of attaching and penetrating the target tissue of the host animal and inducing both cellular and humoral immunity.

the virus particles of this invention are non-viable in that they cannot integrate or replicate in target cells.

In another aspect, the invention provides nucleic acids encoding gp80 polypeptides. The encoded gp80 polypeptides are useful as immunogens to induce immune responses against FeLV. The gp80 polypeptides or the nucleic acids encoding them can be administered to cats.

Another aspect of the invention is a composition of plasmid DNA useful for vaccination. In an embodiment circular plasmid DNA is administered to host animal muscle. In another embodiment maternal antibody or seropositive animals do not interfere with immunization with debilitated FeLV proviral DNA. In another embodiment purified DNA is administered as a single dose with production of non-replicating virus particles within about 2 weeks after injection and up to about 12 months after injection.

Definitions:

An "immunogen" refers to a polypeptide or protein which is "immunogenic," i.e., capable of eliciting an immune response, in this case against FeLV antigens. An immunogenic composition of the invention can be a composition comprising the polypeptide or a recombinant vector which encodes the polypeptide.

The terms "gp80 polypeptide" or "gp80 protein" refer to a truncated form of the FELV gp85 env protein that induces an immune response against FeLV env proteins and which substantially lacks the membrane binding domain of p15E, which is located at the C-terminus of gp85. A gp80 polypeptide of the invention typically, lacks about 50 amino acids from the C-terminus. The precise length of the gp80 polypeptide of the invention, however, is not critical, so long as the membrane binding functions of the p15E protein are substantially lacking and the polypeptide induces an immune response against the native env protein. Means for testing the truncated gp85 proteins of the invention are well known to those of skill and are described in more detail below.

In addition, the precise sequence of the polypeptides of the invention or the sequences encoding them need not be identical and may be "substantially identical" to a sequence disclosed here. As explained below, these variants are specifically covered by the term gp80.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term specifically includes those sequences substantially identical (determined as described below) with a sequence disclosed here and that encode proteins that capable of inducing immune response against FeLV antigens.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Optimal alignment of sequences for comparison can use any means to analyze sequence identity (homology) known in the art, e.g., by the progressive alignment method of termed "PILEUP" (see below); by the local homology algorithm of Smith & Waterman, *Adv. Appl. Math.* 2: 482 (1981); by the homology alignment algorithm of Needleman & Wunsch, *J. Mol. Biol.*, 48:443 (1970); by the search for similarity method of Pearson (1988) *Proc. Natl. Acad. Sci. USA* 85: 2444; by computerized implementations of these algorithms (GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by Higgins (1988) *Gene,* 73:237–244; Corpet (1988) *Nucleic Acids Res.* 16:10881–90; Huang (1992) *Computer Applications in the Biosciences* 8:155–65, and Pearson (1994) *Methods in Molec. Biol.* 24:307–3 1), TreeAlign, MALIGN, and SAM sequence alignment computer programs; or, by inspection. See also Morrison (1997) *Mol. Biol. Evol.* 14:428–441, as an example of the use of PILEUP. PILEUP, creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp (1989) *CABIOS* 5:151–153. The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

Another example of algorithm that is suitable for determining sequence similarity is the BLAST algorithm, which is described in Altschul (1990) *J. Mol. Biol.* 215:403–410. Software for performing BLAST analyses is publicly available through the National Center for Biotechnology Information, http://www.ncbi.nlm.nih.gov/; see also Zhang (1997) *Genome Res.* 7:649–656 (1997) for the "Power-BLAST" variation. This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff(1989) *Proc. Natl. Acad. Sci. USA* 89:10915) alignments (B) of 50, expectation (E) of 10, M=5, N=−4, and a comparison of both strands. The BLAST algorithm performs a statistical analysis of the similarity between two sequences (see, e.g., Karlin (1993) *Proc. Natl. Acad. Sci USA* 90:5873–5787). One measure of similarity provided by the BLAST algorithm is the smallest sum probability (P(N)), which provides an indication of the probability by which a match between two nucleotide or amino acid sequences would occur by chance.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90% and most preferably at least 95%, compared to a reference sequence using the programs described above using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about I molar at pH 7 and the temperature is at least about 60° C.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, COG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

DESCRIPTION OF THE PREFERRED EMBODIMENT

It is estimated that between North America, Western Europe and Japan there is a population of approximately 100 million cats that represent the domestic population and are subject to consideration for health care treatment. Of these animals only 30 percent are presently vaccinated and only 10 percent of the vaccinated population return for boosters, which are mandated by the labeling of most vaccines. That is, priming and sometimes two boosting doses with yearly vaccinations are recommended for most feline pets. The reasons for such a low vaccination and return-visit rate are several: 1) There is a low confidence rate that the vaccine is efficacious and or safe by the customer. 2) It is inconvenient for the customer to return their animal a second or third time over a short period. 3) Many animals are nonhousehold pets or in shelters that do not provide vaccine programs.

In addition to the perception of low efficacy and safety by the customer, as stated above, FeLV vaccine production is hampered by the inability to reproducibly manufacture consistent amounts of FeLV virus and or proteins in cell culture. The invention provides for a means to produce a consistent amount of active immunizing component with a minimal but predictable and measurable amount of contaminating components. The present vaccines available for control of FeLV and associated diseases have shown to be efficacious through the utilization of inactivated or purified subunits that do not involve a live replicating component of the virus but require both priming and boosting doses of vaccine. Thus, an invention that provides a means to deliver a consistent dose of a non-replicating vaccine in a single administration would not only provide a better health care treatment to the animal, but provide a more convenient option to the pet owner. The FeLV proviral DNA composition of this invention is such that it is genetically recombined to a plasmid DNA to allow production of the recombinant DNA in E. coli using standard known procedures in the art. The nature of the recombinant DNA is such that it can easily be accessed and evaluated for consistent sequence and structure by using known molecular biology tools and procedures such as polymerase chain reaction (PCR), restriction fragment polymorphisms and DNA sequencing.

The present invention is to allow a practical and consistent means to manufacture an FeLV vaccine of subgroup A taken from the current cat population which represents a variant in the natural environment not controlled or eliminated by current vaccine programs. Although all three subgroups of FeLV exist in nature, the only subgroup that is commonly found in all natural infections is FeLV-A. The sequence of all three subgroups differ somewhat in homology as well as in specific attenuations that involve deletions, substitutions or insertions within certain regions of the envelope gene (U.S. Pat. No. 5,152,982; Lour, A. S. Vet. Clin. N. Amer. 23:193–211 (1993)). Hypotheses that FeLV-A progresses to FeLV-B after a certain number of rounds of replication and then to FeLV-C over a longer and more persistent infection are well founded based on the percent of FeLV-B and FeLV-C found in nature and mutations in the envelope protein. Subgroup B and C tend to not replicate well in cats without the presence of subgroup A, but are considered to be more pathogenic than subgroup A (Hoover, E. A. and Mullins, J. I. J. Am. Vet Med Assoc. 199:1287–1297, 1991). Despite this fact, FeLV-A remains the only subgroup present in all infections and thus, has been of the greatest concern to incorporate into vaccine development programs. The FeLV-A isolated by BioTrends International Laboratories (BTI-FeLV-A) represents a FeLV of subgroup A as defined by partial nucleotide sequence of the envelope gene and was taken from a cat that had been into a routine clinical visit in Fair Oaks, Calif. small animal clinic. Thus, the proviral DNA described here represents a new isolate of FeLV not yet described and not yet evaluated for ability to be neutralized by prophylactic treatment of cats with any known vaccine regimen.

This invention describes the production of a FeLV DNA that can be used to induce an immune response against FeLV in cats. In some embodiments, the DNA is modified so as to allow production of both gag and env gene products to provide maximum immune response to both conserved and variable epitopes of the virus. In addition, by injection intramuscular (IM) into the muscle of cats the modified proviral DNA can persist and provide a low level of antigen in the form of fully formed but nonreplicating virus particles. The production of virus proteins by muscle cells and the circulating virus particles provide for immune targets to stimulate both humoral and cell mediated responses in the cat.

In addition, the invention provides vaccines using individual proteins or genes from the FeLV genome. A preferred gene to use for this purpose is the env gene. In some embodiments, the full length env protein (gp85) is expressed and used as the vaccine. In preferred embodiments, a truncated form referred to here as gp80 is used. The gp80, truncated form, has advantages over the full length polypeptide because it lacks a those sequences from p15E which are believed to have membrane binding properties (Ramsey, et al., 4th International Retrovirus Research Symposium, Official Program, pg 41).

This invention thus relates to immunogenic compositions capable of eliciting an immunogenic response directed to FeLV. This can be accomplished by administering either the nucleic acids disclosed here or polypeptides encoding them. The encoded polypeptides can be readily designed and manufactured utilizing various recombinant DNA or synthetic techniques well known to those skilled in the art. For example, the polypeptides can vary from the naturally-occurring sequence at the primary structure level by amino acid, insertions, substitutions, deletions, and the like. These modifications can be used in a number of combinations to produce the final modified protein chain. For instance, fusion proteins comprising the polypeptides of the invention fused to various heterologous proteins can be prepares.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring FeLV polypeptides. The nucleotide sequences can be modified according to standard techniques to yield the desired polypeptides, fusion proteins, or fragments thereof, with a variety of desired properties.

Any of a number of other well known cells and cell lines can be used to express the polypeptides of the invention. For instance, prokaryotic cells such as E. coli can be used. Eukaryotic cells include any of a number of mammalian cell lines commonly used to produce recombinant polypeptides. Feline kidney cells and feline embryonic cells are particularly useful for this invention.

The nucleic acids, and polypeptides of the present invention are useful as vaccines, for treating or preventing FeLV infections. Compositions containing the polypeptides or nucleic acids are administered to a subject, giving rise to an immune response against FeLV, which inhibits FeLV infection in the animal. An amount of a composition sufficient to result in this inhibition is defined to be an "immunologically effective dose." In this use, the precise amounts, will of course, depend on the patient's state of health and weight, the mode of administration, and the nature of the formulation. Typically, an immunologically effective dose for a polypeptide of the invention will be between about 1 to about 50 μg/kg body weight, preferably about 5 to about 20 μg/kg body weight. In the case of administering nucleic acids the dose will be between about 5 to about 500 μg/kg body weight, preferably about 50 to about 100 μg/kg body weight.

The polypeptides or nucleic acids of the present invention can be used in pharmaceutical and vaccine compositions that are useful for administration to mammals, particularly cats, to inhibit FeLV infections. The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

The vaccines of the invention contain as an active ingredient an immunogenically effective amount of the polypeptides or nucleic acids as described herein. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as quill-A, cholesterol, aluminum phosphate, aluminum hydroxide, or alum are materials well known in the art.

As noted above, a preferred method is the administration of DNA encoding the polypeptides of the invention. This approach is described, for instance, in Wolff et. al., *Science* 247: 1465–1468 (1990) as well as U.S. Pat. Nos. 5,580,859 and 5,589,466. Several pharmaceutical or prophylactic formulations can be utilized with the purified plasmid DNA of this invention. Plasmid DNA can be prepared in solution or in desiccated form by several methods known to those skilled in the art. More specifically, the sample can be diluted to the desired buffer or DNA concentration directly and packaged directly into receptacles for administration or storage. The sample may also be dialyzed against the desired solution or diluent to be used to administer the product. The purified DNA can be removed from the elution buffer or other solutions by a variety of techniques known to those skilled in the art; typically lyopholization or precipitation of polynucleotide salts in solvents are utilized. In this invention the preferred method is to avoid the use of solvents or other hazardous chemicals to precipitate the DNA. PEG 8000 is the preferred method and is used in a similar manner described above. DNA can then be resuspended in a diluent of other formulation of choice. Although a number of diluents and pharmaceutical/prophylactic formulations are known to those skilled in the art, the diluent is most likely to be high quality water containing physiological concentrations of salt or carbohydrates to remove stinging or burning sensation when administered by standard methods which require penetration of the outer skin surface.

DNA can be stored in suspension or as a salt of PEG pellet at several temperatures ranging from −80° C. to 25° C. Most preferably DNA is resuspended in sterile diluent containing 0.15 M NaCl and 25 mM phosphate buffer pH 7.2.

Although the purified plasmid DNA containing the modified proviral DNA can be delivered to a cat subcutaneously, intramuscular, intraperitoneally, intradermally, intranasally, orally or topologically; the preferred method is by intramuscular injection. The purified DNA can be administered in a volume of 0.05 ml to 2 ml of a physiological sterile saline containing between 0.1 ug to 1 mg of DNA. Most preferable the volume is 0.5 ml–1 ml containing 100–500 ug of plasmid DNA.

The isolated nucleic acid sequences coding for desired polypeptides can also be used to transform viruses which transfect host cells in the susceptible organism. Live attenuated viruses, such as vaccinia viruses are convenient alternatives for vaccines because they are inexpensive to produce and are easily transported and administered. Vaccinia vectors and methods useful in immunization protocols are described in, e.g. U.S. Pat. No. 4,722,848. Other suitable vectors include, but are not limited to, pox viruses, such as, canarypox and cowpox viruses, and other animal viruses.

The present invention is described below. Although these examples describe broadly the methods used, they are not intended to be limited by these examples.

EXAMPLE 1

Isolation of BTI-FeLV-A

BTI-FeLV-A was isolated from a cat that was being treated in a Fair Oaks, Calif.; clinic for an ongoing episode of lymphoreticular related disease (BTI-FeLV-A was deposited with the ATCC under the terms of the Budapest Treaty and has been accorded ATCC designation PTA-1765. The lymphocytes isolated from this cat yielded positive serology for both FeLV and FIV by the Idexx antibody test. Furthermore, when extracts of infected cell material were co-cultivated with Crandel Feline Kidney (CRFK) cells two types of cytopathic effects were observed indicating a feline foamy virus and FeLV. To isolate the FeLV component the virus population was maintained chronically infected CRFK cells; total chromosomal DNA was extracted using QIAamp blood Kit (Qiagen Inc., Chatsworth Calif.). The FeLV proviral DNA sequences that are long terminal repeat minus (ltr–) and integrase minus (int–) can be isolated from total chromosomal DNA or RNA taken from infected cell culture by techniques that are generally known to those skilled in the art. More specifically, FeLV-A specific sequences were then amplified from the purified DNA by the polymerase chain reaction (PCR) using oligonucleotide primers derived from FeLV-A sequences according to Genebank accession number M18247. Amplified regions corresponding to defined regions of FeLV were:

1. 5'-primer for amplification of gag and pro genes (primer FeLV VII)

5'-A GGATCCRCGAAGGAGCTGACGAGCTCGTACTTCG-3'
(SEQ ID NO: 1)
Bam HI 2. 3'-primer for amplification of gag and pro genes (primer FeLV-IV)

5'-A GAATTCCATCTCCTGTTTTGTGTACTTTCTGGCTC-3'
(SEQ ID NO: 2)
EcoRI 3. 5'-primer for amplification of env gene (primer FeLV-V)

5'-A GAATTCGATACTGATATCTCTACGTTCGCTACCTGG-3'
(SEQ ID NO: 3)
EcoRI 4. 3'-primer for amplification of env gene (primer FeLV-VI)

5'-A GCGGCCGCGGGACTAAATGGAATCATACATTAATTGG-3'
(SEQ ID NO: 4)
NotI

PCR was performed on 5 ug of the template DNA using the above primers. Two sets of primers were used, one set consisted of primers FeLV-IV and FeLV-VII for amplifying the region of BTI-FeLV-A genome comprising of gag and pro genes. The second set consisted of primers FeLV-V and FeLV-VI for amplification of the env gene. PCR was performed in DNA Thermocycler using the following parameters. Thirty five cycles total, each cycle consisted of 30 sec at 94C.; 30 sec at 55C.; 30 sec at 72C.; at the end of 35 cycles, reaction contents were maintained at 72C. for an additional 7 minutes, for completion of the ends of the PCR products. The PCR product obtained using primers FeLV-IV/VII was 2.25 kilobase (Kb) in size (fragment 1), containing the engineered restriction sites at both ends as shown in the primer sequence above, i.e., BAM HI site at the 5' end and EcoRI at the 3'-end. The PCR product obtained using primers FeLV-V/VI was 2.34 Kb in size (fragment 2), containing engineered restriction sites as shown in the primer sequence above, i.e., Eco RI at the 5'-end and NotI at the 3' end. These two PCR products were cloned directly into pCRII vector (Invitrogen, Inc., Calif.), according to manufacturer's instructions.

Figure 1:
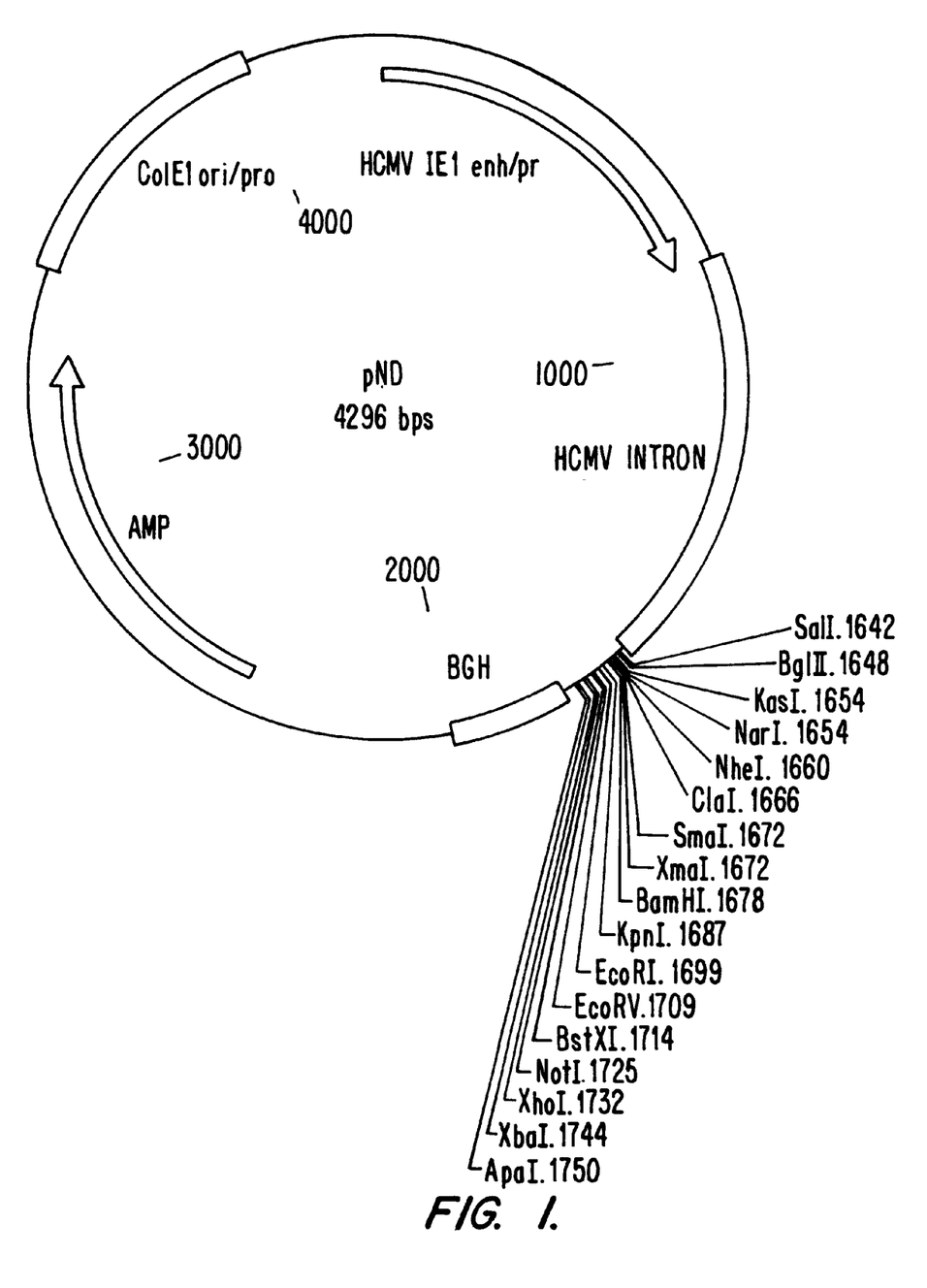
FIG. 1 graphically presents the plasmid DNA vector containing the promoter, insertion site and multiple cloning sites.

Vector pND (FIG. 1, this vector is modified from the vector disclosed in Chapman et al. *Nuc. Acids. Res.* 19:3979–3986 (1991) by adding the bovine growth hormone polyadenylation site described in Pfarr et al. *DNA* 5:115–22 (1986)) was digested with BamHI and NotI enzymes; fragments constituting gag/pro (fragment 1) and env (fragment 2) genes, together representing the complete PCR amplified portion of the FeLV genome were removed from their respective clones in pCRII vector by digest with BamHI+EcoRI and EcoRI and NotI enzymes, respectively. The resulting pieces of DNA were electrophoresed on agarose gel and the DNA bands representing fragment 1 & 2 were excised out of the gel. DNA was purified from excised gel slices by Qiagen Gel Extraction Kit (Qiagen Inc., Chatsworth Calif.). A three-way ligation was then performed which resulted in joining of fragment 1 and 2 at their cohesive ends (3'-end of Fragment 1 joined to 5' end of fragment 2) and insertion of the joined fragments into pND, between BamHI and NotI restriction sites. The resulting plasmid was designated pIK102 (FIG. 2) (ATCC No. 203327, deposited Oct. 7, 1998).

Figure 2:
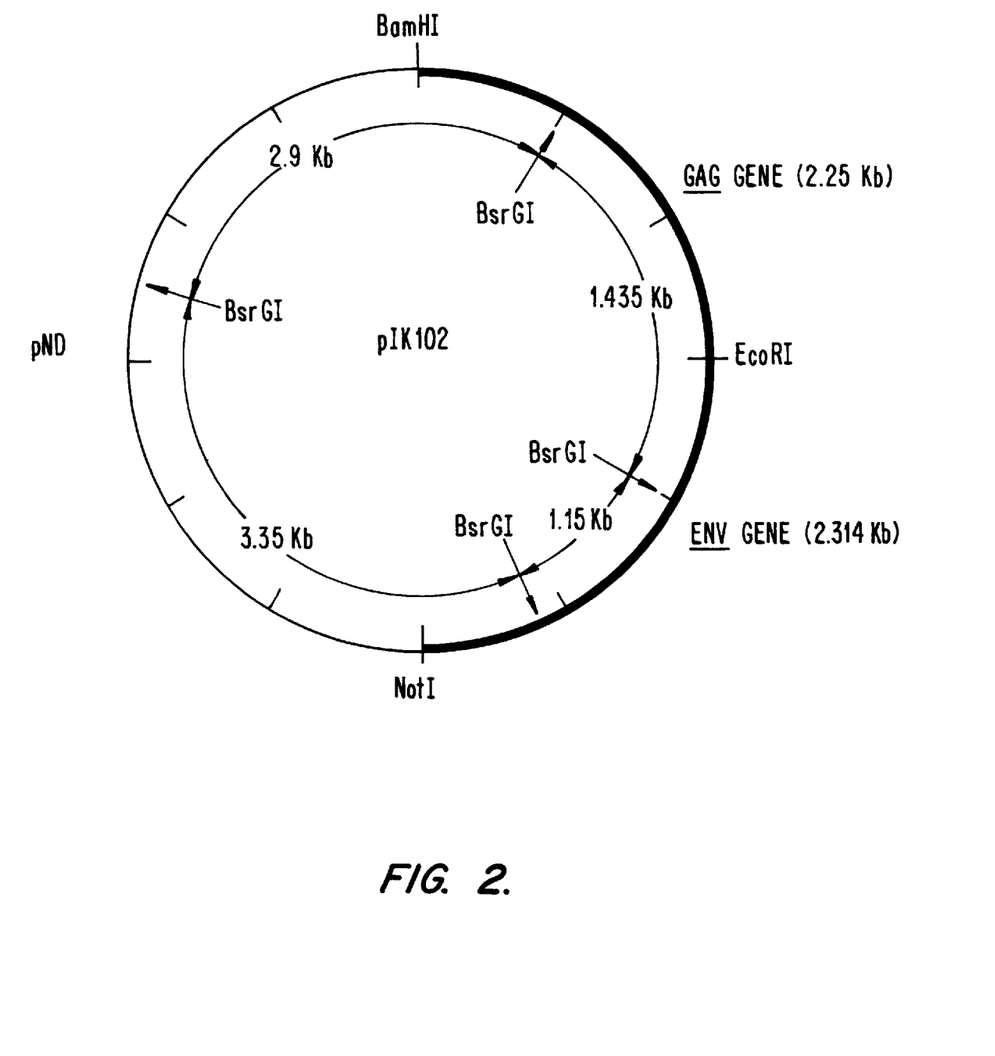
FIG. 2 graphically presents the plasmid DNA containing the truncated form of FeLV proviral DNA.

The resulting modified-proviral DNA has the following features: a) It utilizes a CMV early promoter region located at the 5' end of the gag gene region to drive viral mRNA synthesis. b) The gag gene has been retained intact defined by the primers described above. c) The entire coding region of the env gene has been provided to allow production of both gp70 (external globular region of the envelope protein) and p15E which is the spike or stalk portion of the external envelope protein. d) The 3' LTR region has been completely removed and replaced with poly A addition site that provides a termination signal for mRNA production. e) The polymerase binding site and RNA packaging signals of FeLV are not present.

Because the 3' LTR is absent and because the pol gene has a lethal mutation the proviral DNA does not have the ability to be replicated nor can full length infectious genomic virion RNA be assembled or packaged in the virus particle. However, because the intact gag and env genes can be expressed from this construct, the internal core, matrix and env proteins can assemble in virus particles but are not infectious.

EXAMPLE 2

Purification of FeLV pIK102 plasmid

The FeLV pIK102 plasmid was transformed into *Escherichia coli* HB 101 using standard method described by Maniatis, et. al. Molecular Cloning third edition. The HB 101 pIK102 was grown in Luria Broth Base containing 50 μg/l of ampicillin. After an overnight incubation at 37° C., 200 rpm, the cells were harvested by centrifuging at (5000 rpm), at 4° C. for 30 minutes. The cell pellet was resuspended in STE (0.1 M NaCl, 10 mM Tris, 1.0 mM EDTA, pH 8.0) and centrifuged as described previously. The supernatant was discarded, and the cell pellet was again resuspended in STE and centrifuged. The washed cell pellet was then stored at –80° C. for plasmid purification.

EXAMPLE 3

Inoculation of cats using pIK102 plasmid DNA

Cat inoculation. Specific pathogen free Harlan Sprague Doweling cats to be used in the study were bled the day of vaccination. The cats were then vaccinated with purified plasmid DNA pIK102 in physiological saline solution. The cats received doses of 0 or 200 μg of pIK102 DNA injected intramuscularly, with three cats per treatment group. One group of cats received a 400 μg injection eight weeks after the primary injection. Serum was collected 4, 6, 9, and 18 weeks after the first vaccination. The serum was evaluated by serum neutralization assays and three types of ELISA.

EXAMPLE 4

Detection methods for virus specific antibody and virus protein

ELISA to detect FeLVgp70 in cat sera. In order to detect viral gp70 in the vaccinated cat's sera, affinity-purified gp70 goat antibody was adsorbed to microtiter plates (0.25 μg per well). The serum collected from the cats was diluted 1:5, 1:10, 1:20 and 1:40 in Buffer 3T, and allowed to react with the goat gp70 antibody. The second antibody used to detect gp70 in cat serum was a C11D8 monoclonal antibody (0.6 μg per well). The monoclonal antibody was detected using peroxidase-conjugated goat antimouse IgG. The conjugate had been preabsorbed with cat IgG to reduce nonspecific activity.

ELISA to detect FeLVgp70 antibody in cat sera. To detect antibody to gp70 in the vaccinated cat's sera, FeLV strain FL74 (Seattle) or 3281 (New York subgroup A) was purified by sedimentation, prior to use as the capture antigen. The FeLV strains in PBS with 0.05% sodium azide, pH 7.2, were adsorbed to Immulon 3 microtiter plates (0.25 μg per well) overnight at room temperature. Serum collected from the cats was diluted 1:5, 1:10, 1:20 and 1:40 in Buffer 3T, and allowed to react with the virus for 45 minutes at room temperature. The anti-gp70 in serum samples was detected using peroxidase-conjugated goat anti-cat antibody (Jackson Immunoresearch) that detected both the heavy and light chains, and thus both IgG and IgM were detected. The goat anti-cat conjugate was diluted 1:1000 in buffer 3T, incubated 45 minutes at room temperature, and the plates were washed three times. The conjugate was detected by adding 150 μl per well of OPD substrate. The OPD substrate contained 20 mg in 15 ml substrate buffer and 80 μl of 30%. OPD per microtiter plate. The plates were incubated 6 minutes at room temperature, and the reaction was terminated with 50 μl per well of 2M sulfuric acid. The plates were read at 493 nm using a spectrophotometer.

ELISA to differentiate IgG and IgM anti-gp70 in cat sera. In this assay, the anti-gp 70 was detected as described above, except that goat anti-cat conjugate was not used. Instead, IgG was detected using the monoclonal anti-cat IgG conjugate (KIM2-1A-biotin), and IgM was detected using the monoclonal anti-cat IgM conjugate (CM7-biotin). The conjugates were diluted to 1.0 μg/ml with Buffer 3T, and incubated for 45 minutes at room temperature. ExtrAvidin™ (Sigma, St. Louis, Mo.) was diluted 1:1000 in Buffer 3T and incubated in the plates for 45 minutes at room temperature.

Color was developed, and the reaction was terminated as described above.

EXAMPLE 5

Expression of Gag and Env proteins from pIK102

Figure 3:
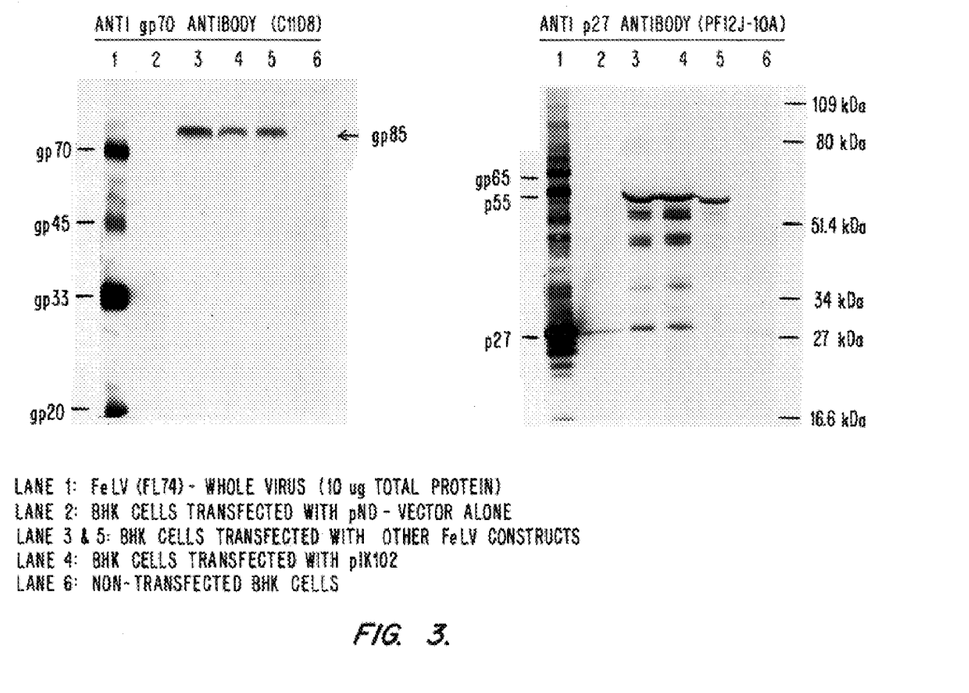
FIG. 3 shows the expression gp70 and p27 gag proteins in transfected BHK cells from recombinant plasmid pIK102.

To test the expression of gag and env gene products, plasmid pIK102 was transfected in BHK-21 cells using Lipofectamine (Life Technologies, Inc., Gaithersburg, Md.), following the manufacturer's instructions. The transfected cells were lysed, lysates were run on SDS-polyacrylamide gel, and proteins were then transferred from gel to PVDF membranes (BioRad, Hercules, Calif.). Membranes with transferred proteins were blotted with either anti-env/anti-gp70 (C11D8) or FeLV anti-gag/anti-p27 (PF12J-10A) monoclonal antibodies (FIG. 3, left and right panels, respectively). Both complete envelope protein (gp85) and gag (p55, p27 and other degradation products) proteins were efficiently expressed in BHK cells transfected with pIK102 (lane 4, anti-env and anti-gag blots). The control cells, that were either non-transfected or transfected with pND, did not express any of these proteins (lanes 2& 6, both blots). Lane 1, FIG. 3 in both anti-env and anti-gag blots displays expression of env and gag gene products, respectively, in FeLV cell free virions. Since FeLV virions contain completely processed env and gag proteins, the banding pattern in lane 1 of both blots is different from lane 4 in each blot which contain whole BHK cell lysates with env and gag protein expressed from pIK102. For example, FeLV virion contain the gp70 component of the env protein, along with some further p33 and gp20 (lane, anti-env blot), whereas lysate from BHK cells transfects with pIK102 expresses only non-processed gp85 envelope protein (anti-env blot, lane 4 arrow). Similarly, FeLV virions contain processed gag gene products with a large proportion of p27 protein and relatively smaller proportion of p55 (lane 1, anti-gag blot), while lysate from BHK cells transfected with pIK102 expressed non-processed gag gene products containing a small proportion of p27, and a relatively larger proportion of p55 (lane 4, anti-gag blot).

In addition, DNA vaccines comprising the pIK102 constructs were administered to cats. DNA was suspended in 1 ml of sterile physiological saline (0.15M NaCl) and injected in the hind quadriceps muscle. FeLV p27 antigen (μg/ml) was tested in the serum of the animals using the ViraChek detection kit (Synbiotics, San Diego, Calif.). All sera were negative for p27 antigen prior to challenge with FeLV.

The results of post-challenge bleeds are shown in Tables 1–3. As can be seen there, vaccination at the dose indicated, followed by boost about two months later, led to a dramatic decrease of p27 antigen in the serum as compared to controls (Table 2). Vaccination without a boost did not inhibit the virus as well (Table 3).

TABLE 1

| | Naive Controls | | | | | |
|---|---|---|---|---|---|---|
| | Cat | 4 weeks post-challenge | 5 weeks post-challenge | 6 weeks post-challenge | 7 weeks post-challenge | 8 weeks post-challenge |
| 1) | A151 | 0.343 | 0.596 | 0.313 | 0.122 | 0.265 |
| 2) | A155 | 1.197 | 1.68 | 1.72 | 1.027 | 3.151 |
| 3) | A137 | 0.811 | 1.45 | 1.45 | 1.733 | 3.117 |

TABLE 2

Gag-deltapol-env, 200 µg, followed by boost 400 µg 4 weeks later

| | Cat | 4 weeks post-challenge | 5 weeks post-challenge | 6 weeks post-challenge | 7 weeks post-challenge | 8 weeks post-challenge | 9 weeks post-challenge | 10 weeks post-challenge | 11 weeks post-challenge | 12 weeks post-challenge |
|---|---|---|---|---|---|---|---|---|---|---|
| 1) | 1175 | 0.203 | 1.15 | 1.64 | 1.117 | 1.237 | 0.881 | 0.598 | 0.296 | 0.371 |
| 2) | 1179 | Negative | Negative | Negative | Negative | Negative | Negative | Negative | Negative | Negative |
| 3) | 1185 | Negative | Negative | Negative | Negative | Negative | Negative | 0.416 | Negative | Negative |

TABLE 3

Gag-deltapol-env, 200 µg, no boost:

| | Cat | 4 weeks post-challenge | 5 weeks post-challenge | 6 weeks post-challenge | 7 weeks post-challenge | 8 weeks post-challenge | 9 weeks post-challenge | 10 weeks post-challenge | 11 weeks post-challenge | 12 weeks post-challenge |
|---|---|---|---|---|---|---|---|---|---|---|
| 1) | GO10 | Trace (<0.03) | 1.53 | Negtive | 1.046 | 2.424 | 2.290 | 1.959 | 0.696 | Negative |
| 2) | GO11 | 0.459 | 0.885 | 0.787 | 0.474 | 2.079 | 3.479 | 1.565 | 2.424 | 0.999 |
| 3) | GO14 | Trace (<0.03) | 0.929 | 1.444 | 0.939 | 2.097 | Negative | 1.062 | Negative | 1.397 |

EXAMPLE 6

Use of a truncated env gene as a DNA subunit vaccine

A truncated env gene lacking 150 base pairs (bp) at the 3' end was PCR amplified from the BTI-FeLV-A isolate. The amplified env gene was cloned into the pND vector described above.

(a) PCR primers:

All PCR primers were designed based on DNA sequence of an FeLV subgroup-A clone; Genebank accession number: M18247.

1. 5'-primer for amplification of truncated env gene:

5'<u>AGAATTC</u>ATCAAGATGGAAAGTCCAACGCAC CC-3' (SEQ ID NO: 5)

EcoRI 2. 3'-primer for amplification of truncated env gene:

5'<u>AGCGGCCGC</u>TTATCACCCATAATGGAGGAAA TTAGGGTTGTAAACC-3' (SEQ ID NO: 6)

Not I (b) Template DNA for PCR:

DNA was isolated and purified from 1×10$^7$ Crandell feline kidney (CrFK) cells, chronically infected with the BTI-FeLV-A I isolate, by the use of QIAamp Tissue/Blood DNA Kit (Qiagen Inc., Chatsworth, Calif.). Concentration of the purified cellular DNA was determined by absorbance at 260 nm.

(c) PCR:

PCR was performed on 5 µg of the template DNA using the above primers. One set of primers was used, it consisted of primers "1" and "2" shown above, for amplifying the region of the genome comprising of the env gene. PCR was performed in DNA Thermoclycler (Perkin Elmer, Foster City, Calif.) using the following parameters:

35 cycles total, each cycle consisted of 30 sec @ 94° C.; 30 sec @ 55° C.; 30 sec @ 72° C.; at the end of 35 cycles, reaction contents were maintained at 72° C. for additional 7 min, for completion of the ends of PCR products.

The PCR product obtained using primers 1 and 2 was 1.8 kilo base (Kb) in size, containing the engineered restriction sites at both ends at shown in the primer sequence above, i.e., EcoRI at the 5'-end, and NotI at the 3'-end. The PCR product was cloned directly into pCRII vector (Invitrogen, Inc., Calif.), according to manufacturer's instructions.

Figure 4:
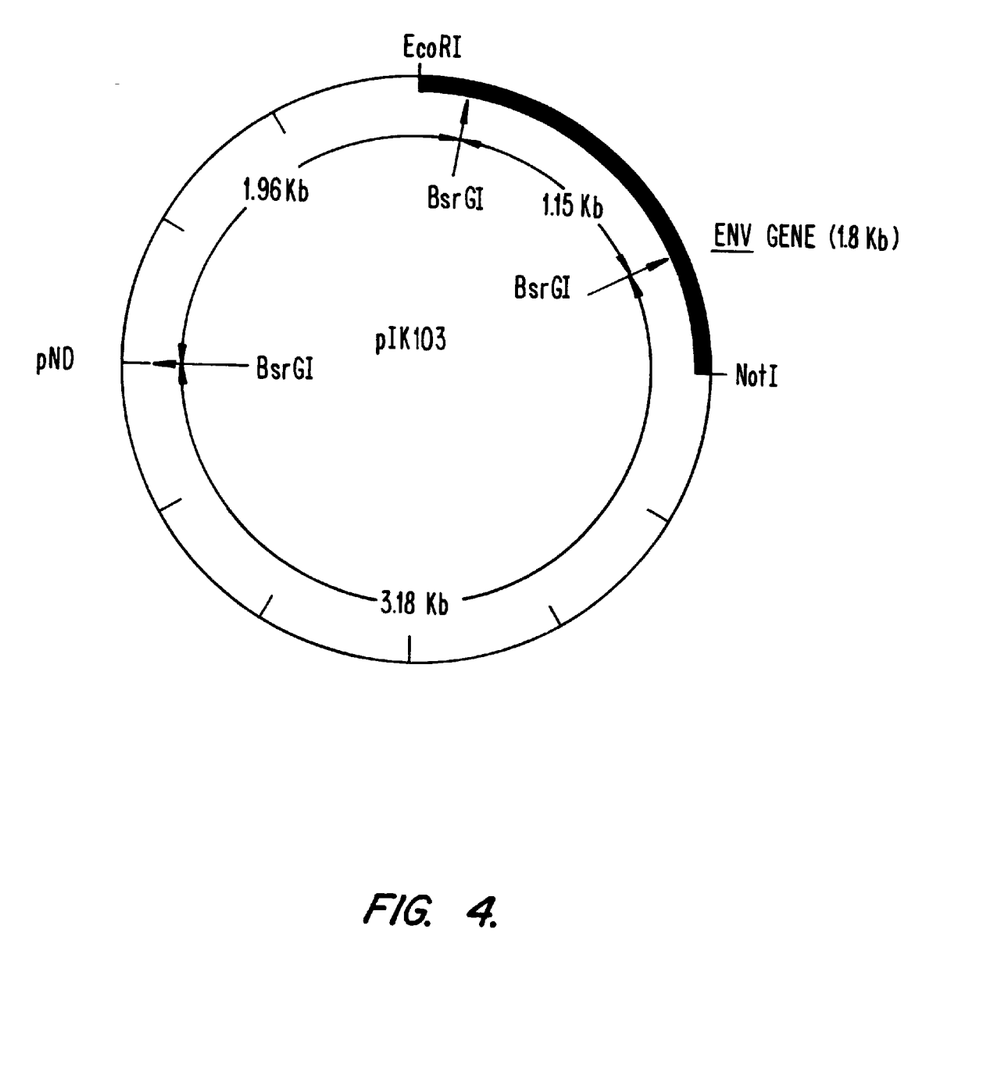
FIG. 4 graphically presents the plasmid pIK103.

(d) Cloning PCR amplified fragments into mammalian expression vector, pND:

Fragment constituting the truncated env was removed from pCRI vector by digestion with EcoRI and NotI enzymes. The resulting DNA fragments were resolved by agarose gel electrophoresis and the DNA fragment representing the truncated env gene was excised out of the agarose gel and purified by Qiagen Gel Purification Kit (Qiagen Inc., Chatsworth, Calif.). Vector pND as digested with EcoRI and NotI enzymes, and the DNA fragment representing env gene was inserted into pND, between EcoRI and NotI restriction sites. The resulting plasmid was designated pIK103 (pIK103 was deposited with the ATCC under the terms of the Budapest Treaty and has been accorded ATCC designation PTA-1766). Plasmid map is shown in FIG. 4; sites for the restriction enzyme BsrGI are shown. The enzyme BsrGI cuts the plasmid pIK103 at three sites. Two of the sites are within the gp70 region of the env gene, which yield a 1.15 Kb fragment upon digestion with BsrGI enzyme indicating that the clone contains FeLV env gene.

This construct can be administered in the same manner as the construct described in Example 5 to provide an immunologically effective dose.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid comprising BTI-FeLV-A env coding sequences.

2. The isolated nucleic acid of claim 1 further comprising FeLV gag coding sequences.

3. The isolated nucleic acid of claim 2, wherein the FeLV gag coding sequences are from BTI-FeLV-A.

4. The isolated nucleic acid of claim 1, wherein the env coding sequence encodes a gp85 polypeptide.

5. The isolated nucleic acid of claim 1, wherein the env coding sequence encodes a gp80 polypeptide.

6. The isolated nucleic acid of claim 5, wherein the env coding sequence is amplified by primers which selectively hybridize to the same subsequence in the FeLV genome as primers having the following sequences:

5'AGAATTCATCAAGATGGAAAGTCCAACGCACCC-3' (SEQ ID NO: 5) and
5'AGCGGCCGCTTATCACCCATAATGGAGGAAATTAGGGTTGTAAACC-3' (SEQ ID NO: 6).

7. A vector comprising the isolated nucleic acid of claim 1.

8. The isolated nucleic acid of claim 1, further comprising a CMV early promoter, wherein viral RNA synthesis is directed by the CMV promoter.

9. The isolated nucleic acid of claim 1, further comprising a BTI-FeLV-A pol gene, wherein the pol gene comprises a lethal mutation.

10. The isolated nucleic acid of claim 1, wherein a BTI-FeLV-A 3' LTR is not present in the nucleic acid.

11. The isolated nucleic acid of claim 1, wherein the nucleic acid is pIK102.

12. A method of immunizing a cat against feline leukemia, the method comprising administering the nucleic acid of claim 1 to a cat.

13. A vaccine for immunizing a cat against feline leukemia virus, the vaccine comprising the nucleic acid of claim 1.

14. An isolated nucleic acid encoding FeLV gp80 polypeptide.

15. The isolated nucleic acid of claim 14, wherein the FeLV gp80 polypeptide is from BTI-FeLV-A.

16. The isolated nucleic acid of claim 15, wherein the env coding sequence is amplified by primers which selectively hybridize to the same subsequence in the FeLV genome as primers having the following sequences:

5'AGAATTCATCAAGATGGAAAGTCCAACGCACCC-3' (SEQ ID NO: 5) and
5'AGCGGCCGCTTATCACCCATAATGGAGGAAAT TAGGGTTGTAAACC-3' (SEQ ID NO: 6).

17. A vector comprising the isolated nucleic acid of claim 14.

18. The isolated nucleic acid of claim 17, further comprising a CMV early promoter, wherein viral RNA synthesis is directed by the CMV promoter.

19. The isolated nucleic acid of claim 18, wherein the nucleic acid is pIK103.

20. The method of claim 12, further comprising administering a nucleic acid of claim 2.

21. The method of claim 20, wherein the nucleic acid is from BTI-FeLV-A.

22. The method of claim 12, wherein said nucleic acid further comprises a CMV early promoter.

23. The method of claim 12, further comprising a BTI-FeLV-A pol gene.

24. The method of claim 12, wherein a BTI-FeLV-A 3' LTR is not present in the nucleic acid.

25. A vaccine of claim 13, further comprising an FeLV gag coding sequence.

26. The vaccine of claim 25, wherein the FeLV gag coding sequence is from BTI-FeLV-A.

27. The vaccine of claim 13, wherein said nucleic acid further comprises a CMV early promoter.

28. The vaccine of claim 13, further comprising a BTI-FeLV-A pol gene, wherein the pol gene comprises a lethal mutation.

29. The vaccine of claim 13, wherein a BTI-FeLV-A 3' LTR is not present in the nucleic acid.

30. The vaccine of claim 13, wherein the nucleic acid of claim 1 encodes a gp80 polypeptide.

31. A vaccine for immunizing a cat against feline leukemia virus, the vaccine comprising a plasmid vector comprising a nucleic acid of claim 1.

32. A vaccine of claim 31, wherein the plasmid vector further comprises an FeLV gag coding sequence.

33. A vaccine of claim 31, wherein the plasmid vector further comprises a BTI-FeLV-A pol gene.

34. A vaccine of claim 31, wherein the plasmid vector is pIK102.

35. A vaccine of claim 31, wherein the plasmid vector is pIK103.

36. The isolated nucleic acid of claim 1, wherein the nucleic acid is pIK103.

* * * * *

SEQUENCE LISTING

<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:5' primer
      for amplification of gag and pro (primer FeLV-VII)

<400> SEQUENCE: 1
aggatcctcg aaggagctga cgagctcgta cttcg                        35

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:3' primer
      for amplification of gag and pro genes (primer FeLV-IV)

<400> SEQUENCE: 2
agaattccat ctcctgtttt tgtgtacttt ctggctc                      37

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence:5' primer
      for amplification of env gene (primer FeLV-V)

<400> SEQUENCE: 3
agaattcgat actgatatct ctacgttcgc tacctcc                      37

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:3' primer
      for amplification of env gene (primer FeLV-VI)

<400> SEQUENCE: 4
agcggccgcg ggactaaatg gaatcataca tttaattgg                    39

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:5' primer
      for amplification of env gene

<400> SEQUENCE: 5
agaattcatc aagatggaaa gtccaacgca ccc                          33

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:3' primer
      for amplification of truncated env gene

<400> SEQUENCE: 6

```
agcggccgct tatcacccat aatggaggaa attagggttg taaacc          46
```